United States Patent
Gleich

(10) Patent No.: US 9,364,165 B2
(45) Date of Patent: Jun. 14, 2016

(54) APPARATUS AND METHOD FOR MOVING AND ACTIVATING AN ACTIVE AGENT

(75) Inventor: Bernhard Gleich, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 308 days.

(21) Appl. No.: 13/392,536

(22) PCT Filed: Sep. 6, 2010

(86) PCT No.: PCT/IB2010/053990
§ 371 (c)(1),
(2), (4) Date: Feb. 27, 2012

(87) PCT Pub. No.: WO2011/030271
PCT Pub. Date: Mar. 17, 2011

(65) Prior Publication Data
US 2012/0152262 A1  Jun. 21, 2012

(30) Foreign Application Priority Data
Sep. 14, 2009 (EP) .................................. 09170211

(51) Int. Cl.
*A61B 19/00* (2006.01)
*A61K 51/00* (2006.01)
(Continued)

(52) U.S. Cl.
CPC ................. *A61B 5/05* (2013.01); *A61B 5/0515* (2013.01); *A61B 5/06* (2013.01); *A61B 5/4839* (2013.01);
(Continued)

(58) Field of Classification Search
CPC ......... A61N 2/02; A61N 1/403; A61N 2/004; A61N 2005/1051; A61B 5/05; A61B 5/0515; A61B 5/06; A61B 19/22; A61B 2019/2257; A61B 5/4839; A61J 3/07
USPC .............................. 600/9, 12, 14, 13; 128/899
See application file for complete search history.

(56) References Cited

U.S. PATENT DOCUMENTS 7,300,452 B2 * 11/2007 Gleich .......................... 607/105
2004/0050394 A1    3/2004 Jin
(Continued)

FOREIGN PATENT DOCUMENTS

DE          10151778        5/2003
JP        2004050394 A      2/2004
(Continued)

OTHER PUBLICATIONS

B. Gleich, et al., "Tomographic Imaging using the Nonlinear Response of Magnetic Particles", Nature, vol. 435, Jun. 30, 2005; doi: 10/1038, pp. 1214-1217.

*Primary Examiner* — Charles A Marmor II
*Assistant Examiner* — Joshua D Lannu

(57) ABSTRACT

The present invention relates to an apparatus for moving a target element which comprises a magnetic material and an active agent, through an object, placing the target element at a predetermined position within the object and activating the active agent. The apparatus comprises: a selection unit comprising a selection field signal generator unit and selection field elements, such as selection field magnets or coils, for generating a magnetic selection field having a pattern in space of its magnetic field strength such that a first sub-zone having a low magnetic field strength and a second sub-zone having a higher magnetic field strength are formed in a field of view, a drive unit comprising a drive field signal generator unit and drive field coils for changing the position in space of the two sub-zones in the field of view (28) by a magnetic drive field unit so that the magnetization of the magnetic material changes locally, and a control unit for controlling the signal generator units to generate and provide control currents to the respective field coils to generate appropriate magnetic fields for moving the target element through the object in a direction instructed by movement commands, for placing the target element at the desired position within the object and for activating the active agent when the target element has reached the desired position.

8 Claims, 7 Drawing Sheets

(51) Int. Cl.
   *A61B 5/05*   (2006.01)
   *A61B 5/06*   (2006.01)
   *A61B 5/00*   (2006.01)
   *A61J 3/07*   (2006.01)
   *A61N 5/10*   (2006.01)

(52) U.S. Cl.
   CPC . *A61B 19/22* (2013.01); *A61J 3/07* (2013.01); *A61B 2019/2257* (2013.01); *A61N 2005/1051* (2013.01)

(56) References Cited

U.S. PATENT DOCUMENTS

| | | | |
|---|---|---|---|
| 2005/0025971 A1* | 2/2005 | Cho et al. | 428/403 |
| 2006/0211939 A1* | 9/2006 | Gleich | 600/410 |
| 2007/0196281 A1* | 8/2007 | Jin et al. | 424/9.34 |
| 2007/0231393 A1* | 10/2007 | Ritter et al. | 424/489 |
| 2007/0232899 A1 | 10/2007 | Bill et al. | |
| 2009/0054722 A1 | 2/2009 | Sugano et al. | |
| 2009/0082611 A1* | 3/2009 | Levy et al. | 600/9 |
| 2009/0093551 A1* | 4/2009 | Bhatia et al. | 514/773 |

FOREIGN PATENT DOCUMENTS

| | | |
|---|---|---|
| JP | 2006128160 A | 5/2006 |
| JP | 2007110278 A | 4/2007 |
| JP | 2007232899 A | 9/2007 |
| WO | WO2006128160 | 11/2006 |
| WO | WO2007110278 | 10/2007 |
| WO | WO2008145377 | 12/2008 |

\* cited by examiner

APPARATUS AND METHOD FOR MOVING AND ACTIVATING AN ACTIVE AGENT

FIELD OF THE INVENTION

The present invention relates to an apparatus and a method for moving a target element, which comprises a magnetic material and an active agent, through an object, placing said target element at a predetermined position within the object and activating the active agent. Further, the present invention relates to a computer program for implementing said method on a computer and for controlling such an apparatus.

BACKGROUND OF THE INVENTION

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e. g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

The MPI technique explained above can be applied for different applications especially in human or veterinary medicine. An interesting application would also be in the field of brachytherapy or other local therapeutical applications, which the above mentioned MPI technique has not been used for so far.

Brachytheraphy is a form of radiotherapy wherein radioactive sources (often called "radioactive seeds") are placed inside the body of a human or an animal for the treatment of, for example, prostate or cervical cancer. Within this method small radioactive seeds are implanted directly into the tumor region in order to radioactively irradiate the tumor tissue. Therefore, brachytherapy is used for internal radiation of body tissues, wherein the radiation is only limited to region of the tumor tissue itself.

Such a brachytherapy treatment method and system is, for example known from WO 2008/145377 A1. With this method the radioactive seeds are implanted into the body through hollow treatment channels, which is a common technique in state of the art brachytherapy methods. The placement of the hollow treatment channels and the amount of radiation dose to be emitted is planned before the surgery in a special treatment plan.

The state of the art brachytherapy is an invasive method which requires a complicated surgery for the implantation of the radioactive seeds. Typical problems which occur with these methods are usually the difficulty in the planning step to exactly define the position of the seeds and the amount of radiation dose to be emitted in order not to affect healthy tissue surrounding the tumor to be treated. Furthermore, it is disadvantageous with brachytherapy methods known in the art that a second surgery is required after the therapy in order to remove the implanted radioactive seeds again.

Also other medical applications are known which are similar to the above-mentioned brachytherapy method, wherein a drug or medicine has to be accurately placed at a very specific place or limited region within the body. Especially within therapeutical treatments of strokes this locally limited medication is an interesting and difficult task. According to state of the art techniques this is usually done, similar to known brachytherapy methods, by very accurately injecting or implanting the drug or medication directly to the desired position. Again, reliable non-invasive methods are so far not known for this kind of applications so that the above-mentioned methods often require complex, time-consuming and even dangerous surgical interventions within the treated object.

SUMMARY OF THE INVENTION

It is an object of the present invention to provide an improved apparatus and method for non-invasively and accurately treating a locally limited area within an object, in particular for the application in brachytherapy or stroke treatments.

In a first aspect of the present invention, an apparatus is presented comprising:

selection means comprising a selection field signal generator unit and selection field elements, in particular selection field magnets or coils, for generating a magnetic selection field having a pattern in space of its magnetic field strength such that a first sub-zone having a low magnetic field strength and a second sub-zone having a higher magnetic field strength are formed in a field of view, drive means comprising a drive field signal generator unit and drive field coils for changing the position in space of the two sub-zones in the field of view by means of a magnetic drive field so that the magnetization of the magnetic material changes locally, and control means for controlling said signal generator units to generate and provide control currents to the respective field coils to generate appropriate magnetic fields for moving the target element through the object in a direction instructed by movement commands, for placing the target element at the desired, predetermined position within the object and for activating the active agent when the target element has reached said desired position.

In a further aspect of the present invention, a corresponding method is presented.

In a further aspect of the present invention a corresponding target element for the use in the above-mentioned apparatus is presented, wherein said target element comprises a magnetic material and an active agent wherein said active agent can be activated by means of a magnetic field.

In still a further aspect of the present invention, a computer program is presented comprising program code means for causing a computer to control the apparatus according to the present invention to carry out the steps of the method according to the present invention when said computer program is carried out on the computer.

Preferred embodiments of the invention are defined in the dependent claims. It shall be understood that the claimed target element, the claimed method and the claimed computer program have similar and/or identical preferred embodiments as the claimed apparatus and as defined in the dependent claims.

It has been recognized by the inventors that the major limitation of known brachytherapy and stroke treatments, the complex, time-consuming and invasive surgery, can be overcome by the presented MPI technology. Hence, the inventors of the present invention have found a solution to use parts of a known MPI apparatus and method by adding control means in order to being able to move a target element, which comprises a magnetic material and an active agent, through an object in a direction instructed by movement commands, to place said target element at a desired position and to activate the active agent when the target element has reached said desired (predetermined) position. In particular, some (or all) of the field coils of the known MPI apparatus are used for generating the appropriate magnetic fields, wherein the newly developed control means is adapted for controlling the respective signal generator units to generate and provide control currents to the respective field coils to generate appropriate magnetic fields for moving the target element through the object and activating the active agent of the target element.

Hence, the present inventors have found an apparatus and a method by use of which active agents, such as e.g. radioactive seeds or medications, can be accurately and non-invasively placed within an object and which then can be activated by means of a magnetic field. The meaning of "active agent" as defined in the present invention comprises any medical, pharmaceutical, physical or radioactive agent or substance.

This technique is especially advantageous for the use in brachytherapy and stroke treatments, wherein the necessary radioactive seeds or lysis drugs can be very accurately placed and locally activated by the help of the presented apparatus. With the ability of MPI to track objects such as a target element, a placement of said target element using an intra-arterial injection becomes feasible.

In contrast to known brachytherapy or stroke treatments, as explained above, the presented MPI apparatus and method allow a very exact locally limited treatment within an object without harming or interfering any unwanted surrounding region. The treatment is non-invasive and in case of a human or animal patient much more comfortable for the patient since no complicated surgical intervention is necessary. Furthermore, the procedure using an apparatus according to the present invention is much faster than methods known in the art, since the magnetic fields can be modified very fast so that the target element including the magnetic material and the active agent can be moved through the object and placed at the desired position in a very short time. Furthermore, in case of a human or animal patient the active agent is together with the target element transported through the arteries and veins, so that every desired point within the body of the patient can be easily and exactly reached. This is, compared to method known in the art, where the medications or the radioactive seeds need to be implanted during a complicated surgical intervention, a great advantage. The planning procedure is also enormously facilitated and the accuracy of the placement is increased.

Even in case a target element gets placed at a wrong position, the position can be easily corrected using the magnetic fields within the MPI apparatus according to the present invention. Furthermore, the application of such target elements is, concerning security reasons, very reliable and safe since the active agent is not activated before the target element has reached its desired position, so that the case where the medication or the radioactive seeds develop their effect at a wrong position cannot happen.

Thus, the present invention proposes an apparatus and a method which can be used in particular for applications of brachytherapy and stroke treatments, which is non-invasive, therefore convenient for the patient and fast and easy to apply.

According to a preferred embodiment, actuation means are provided for changing the position in space of the two sub-zones in the field of view by means of a magnetic field for so long and/or with such a frequency that the magnetic material of the target element in the field of view is heated, so that the active agent of the target element is locally activated. This means that by applying a magnetic frequency field, preferably a radio-frequency (RF) field, the magnetic material comprised in the target element is forced to oscillate. When, due to the RF field, the position in space of the first sub-zone is changed, the magnetization of the magnetic material of those target elements which are situated in the first sub-zone or which migrate from the first to the second sub-zone or vice versa, is changed. Due to this change of magnetization, heat losses occur, for example, due to known hysteresis effects or hysteresis-like effects in the magnetic material, due to the initiation of particle movements or due to other frictional effects, so that the temperature of the whole target element is increased. Because only a comparatively small amount of heat is produced when the magnetization is changed only once, the frequency of the RF field needs to be comparatively high in order to activate the active agent. Apart from the frequency of the RF field, the total heating power also depends on the amplitude of the RF field, the magnetic material within the target element and the size of the target element, respectively the size or the amount of the magnetic material.

If the active agent is for example protected by a coating, the coating may melt or liquefy due to the heating, so that the active agent is activated, respectively relieved from its protection coating and can penetrate into the desired tissue enabling a local therapy. Due to the properties of the MPI system the activation of the active agents can be performed very selectively and accurately. The magnetic frequency field, which is applied to activate the active agent, does not necessarily need to be precisely focused onto the desired target element, since only the magnetic material of the target elements which are placed in the FFP are forced to oscillate and therefore heated. Target elements which are outside the FFP, are under the influence of a higher magnetic field strength, such that the magnetic material in those areas is in the state of saturation and therefore not forced to oscillate by the applied RF field. Thus, the active agent can be activated very selectively and target elements which are not correctly placed do not harm or influence the treatment in a negative way.

According to another preferred embodiment, actuation means are provided for generating a rotating magnetic field in the field of view so that the active agent is separated from the target element due to rotating forces. By applying a rotating magnetic field, fluid flows of more than 10 m/s can be generated around the target element. In this way the target element is forced to rotate very fast so that the active agent is separated from the target element due to occurring rotational forces. This represents a different actuation technique than explained above, where the magnetic material is liquefied due to heat in order to activate the active agent. A still further possibility to activate the active agent is by applying magnetically driven motors, which for example rely on magnetostriction, in order to actively move the active agent out of the target element.

According to another preferred embodiment, focus means are provided which comprise a focus field signal generator unit and focus field coils for changing the position in space of the field of view by means of a magnetic focus field. Such a focus field has the same or a similar spatial distribution as the drive field. The focus field is basically used to move the position of the field of view. This is especially necessary since the field of view has a very limited size so that, if the target element needs to be moved over a longer distance within the object, the focus field needs to change the position in space of the field of view in order to actively move and track the target element over its entire path until it has reached its desired position. In other words, the focus field replaces the active mechanical movement of the object. This means that in case of a human patient the patient would need to be moved physically in order to move the field of view if no focus field means are provided.

Same or even better as the magnetic drive field coils the magnetic focus field coils can be used for the movement of the target element through the object. These coils are able to generate sufficiently homogeneous fields in various directions at a sufficiently high speed and with sufficiently large field strengths that are required for the movement of the target element. The use of these focus field coils therefore provides a high flexibility since they can be generated in any direction.

As already mentioned above, the focus field has the same or a similar spatial distribution as the drive field. It is even possible to use the same magnetic coils as the coils used to generate the magnetic drive field. The basic difference is that the frequencies are much lower (e.g. <1 kHz, typically <100 Hz) for the focus field than for the drive field, but the amplitudes of the focus field are much higher (e.g. 200 mT compared to 20 mT for the drive field).

According to another embodiment of the present invention, the above-mentioned actuation means are realized by said drive means or said focus means. Since, as already mentioned above, the means for generating the drive means or the focus means are very similar, both means can be used to generate the above-mentioned magnetic frequency field which is used to heat the magnetic material within the target element in order to activate the active agent.

According to a still further embodiment the apparatus further comprises:

receiving means which comprise at least one signal receiving unit and at least one receiving coil for acquiring detection signals, which detection signals depend on the magnetization in the field of view, which magnetization is influenced by the change in the position in space of the first and second sub-zone, and processing means for processing the detection signals acquired when appropriate magnetic fields are applied for determining the position of the target element within the object from the processed detection signals. By using the receiving means and the principles of the MPI system, the target element can be localized and visualized by the help of the acquired detection signals. The movement and the localization of the target element can thus be done with the apparatus according to the present invention alternately and almost simultaneously without additional equipment, such as additional hardware for localization, e.g. a camera system or an x-ray system. For the localization the known MPI principles of imaging magnetic particles within an object, as for instance described in the above-mentioned documents, are applied. This means, that the control unit then generates control commands for the signal generator units to generate and provide control currents to the respective field coils to generate appropriate magnetic fields for imaging the target element.

This is especially advantageous since it enables the apparatus and method according to the present invention to easily check the correct movement and position of the target element during its movement through the object without the use of another imaging modality, such as x-ray or CT. Since no x-ray or CT is needed it also reduces the x-ray dosage for the patient and furthermore no additional hardware is required for this functionality.

Since the signals can be very accurately detected and acquired by the receiving means, the target element can be reliably positioned and the defined position can easily be checked and corrected if necessary.

As already mentioned, the target element itself which is used in the above-described apparatus and method preferably comprises a magnetic material and an active agent wherein said active agent can be activated by means of a magnetic field. The active agent is thereby for example a lysis drug or a radioactive seed. On the other hand it has to be noted that the active agent can also be any other substance. It is furthermore preferred that the active agent is arranged in the inner part of the magnetic material, in the coating surrounding the magnetic material or in a matrix together with the magnetic material. If the active agent is arranged in the inner part of the magnetic material, the magnetic material has the function of isolating the active agent from the exterior, so that, for example, in case of a radioactive seed the target element does not irradiate the radioactive radiation before the radioactive seed is activated, respectively before the magnetic coating material is liquefied due to the heating.

If the active agent is arranged in a matrix together with the magnetic material, the matrix can for example be made of a lipid which melts due to the heating. In case of a radioactive material, the material is within the matrix distributed more homogenously over the target element and the ionizing radiation can penetrate the tissue. 71 Ge is the most promising candidate for the radioactive isotope, as it is efficiently shielded by iron (K-edge) and has a low penetration depth in tissue making it suitable for a local therapy. In case of a drug, the chemical diffuses out of the target element after the magnetic coating material is liquefied or melted.

Furthermore, it has to be noted that the size of the target element plays a decisive role. On the one hand the target element can be moved faster the larger the target element is, respectively the more magnetic material is included into the target element. It is also easier to track the target element the larger it is. On the other hand, since in case of a human patient, the target element is moved through the veins and arteries, the target element cannot exceed a specific size of 1 mm. Sizes of 70-150 µm have shown to be especially suitable.

Generally different shapes of the target elements are possible. According to a further preferred embodiment of the present invention, the target element has a spherical, ellipsoidal, helical, rectangular, rod-like or cube-like form. The advantage of realizing the target element as a thin rod is that it can, due to its geometric form, contain a great amount of magnetic material and still blocking of an examined vessel can be avoided as long as the diameter of the vessel is greater than the diameter of the rod. On the other hand a helical form of the target element is also very suitable since in this case the target element can be moved using a rotating magnetic field as mentioned above. The movement direction is in such a case orthogonal to the rotating plane of the magnetic field.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 3. In particular, two embodiments of an MPI scanner for medical diagnostics will be described. The similarities and differences between the two embodiments will be pointed out.

Figure 1:
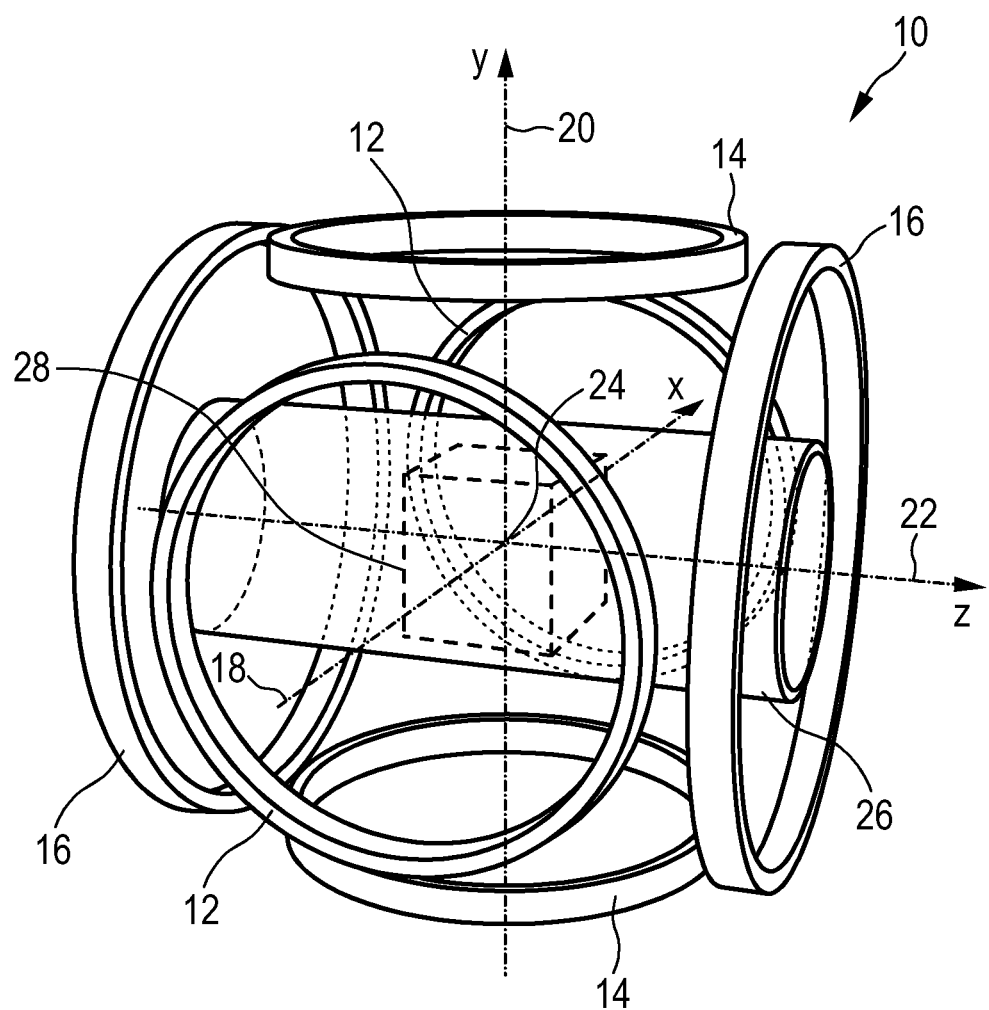
FIG. 1 shows a first embodiment of an MPI apparatus.
Figure 2:
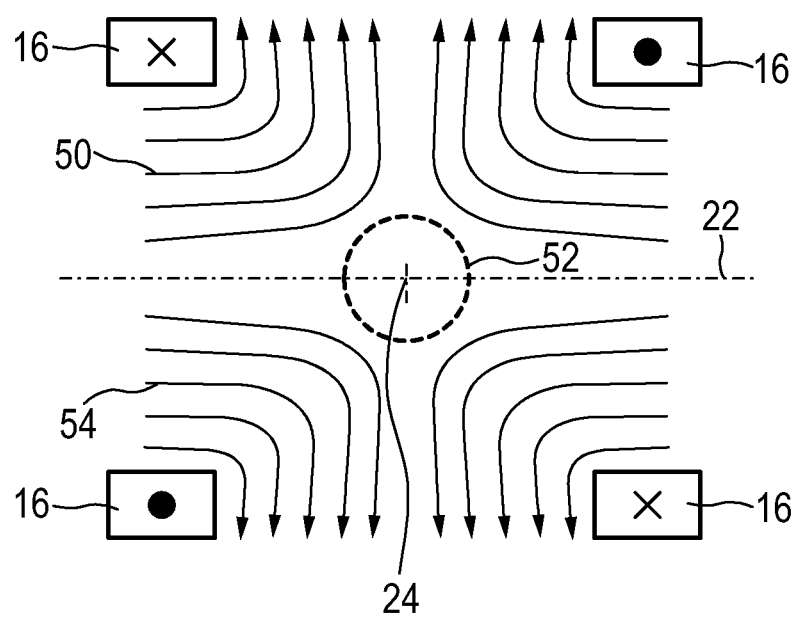
FIG. 2 shows an example of the selection field pattern produced by an apparatus as shown in FIG. 1.
Figure 3:
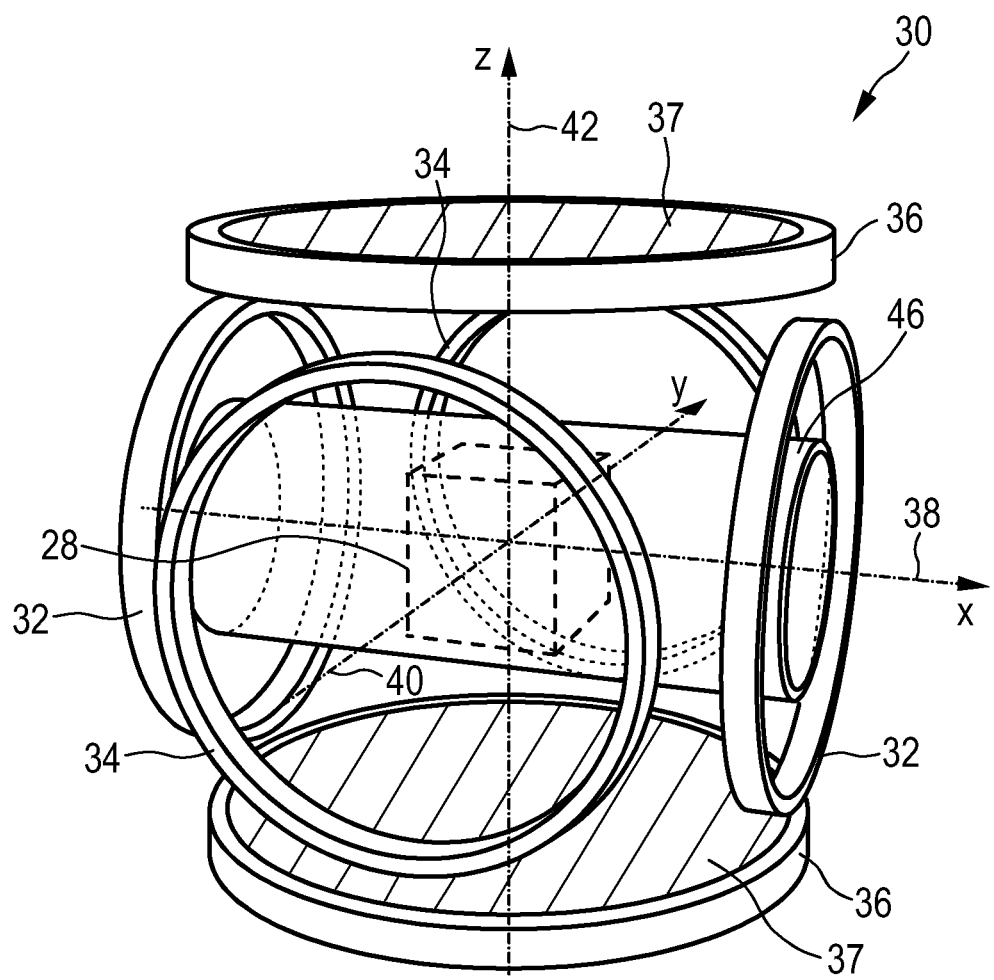
FIG. 3 shows a second embodiment of an MPI apparatus.

It has to be noted that the two embodiments of the MPI scanner shown in FIGS. 1 to 3 also include features which are not all necessarily needed in the apparatus and method according to the present invention. These three figures are meant to give the reader an understanding of the basic MPI principles. For example the receiving and the processing means, which are used for acquiring detection signals and for reconstructing image data thereof, can be included, but are not obligatory according to the present invention. Nevertheless, an informal description of the data acquisition is given in the following. Also the above mentioned and later described focus means are not obligatory for the present invention.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current-$I^S$ is made to flow through the $z^-$-coil. The z-coil pair 16 then acts as an anti-parallel circular coil pair.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of magnetic material, respectively magnetic particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic material, which is according to the present invention part of a target element 60, 70, in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic material in the field of view 28 and thereby information about the spatial distribution of the target elements 60, 70 in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3+I^F_3+I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The embodiment 10 of the MPI scanner may include one further pair, preferably three further pairs, of parallel circular coils, again oriented along the x-, y-, and z-axes. These coil pairs, which are not shown in FIG. 1, serve as receive coils. These receive coils are only needed in the present invention if receiving signals have to be acquired and the acquired data needs to be imaged. This is however not always the case, since moving and placing the target element and activating the active agent are the main purposes of the present invention.

However, if receiving coils are provided, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic material at a magnetic field strength of 80 A/m and a gradient (in a given space direction) of the field strength of the magnetic selection field amounting to $50\times10^3$ A/m$^2$, the first sub-zone 52 in which the magnetization of the particles is not saturated has dimensions of about 1 mm (in the given space direction).

The patient's volume of interest is according the present invention supposed to contain at least one, preferably a greater amount of target elements 60, 70, which comprise a magnetic material 62, 72 and an active agent 61, 71. Theoretically only one target element would be enough if only a small drug or radioactive dosage is needed. However, for practical reasons usually a greater amount of target elements 60, 70 is provided since some target elements 60, 70 might get lost within the body. The loss of some target elements 60, 70 is however not dangerous for the patient, since the active agents 61, 71 of these elements are not activated by the magnetic RF field.

The target elements 60, 70 are positioned in the volume of interest especially prior to a therapeutic and/or diagnostic treatment of, for example, a tumor, e.g. by means of a liquid comprising the target elements 60, 70 which is injected into the body of the patient (object) or otherwise administered, e.g. orally, to the patient.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic material 62, 72 within the target elements 60, 70 in the patient. As the applied RF field changes, the resulting magnetization changes too, though it responds nonlinearly to the applied RF field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the target elements 60, 70 located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic material 62, 72 within the target elements 60, 70 in the scanner's field of view 28 as a result of the non-linearity of the magnetization characteristics.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0 = 2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 28 that fits into the bore 46 has an edge length of $120$ mm/$\sqrt{2} \approx 84$ mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which an RF coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
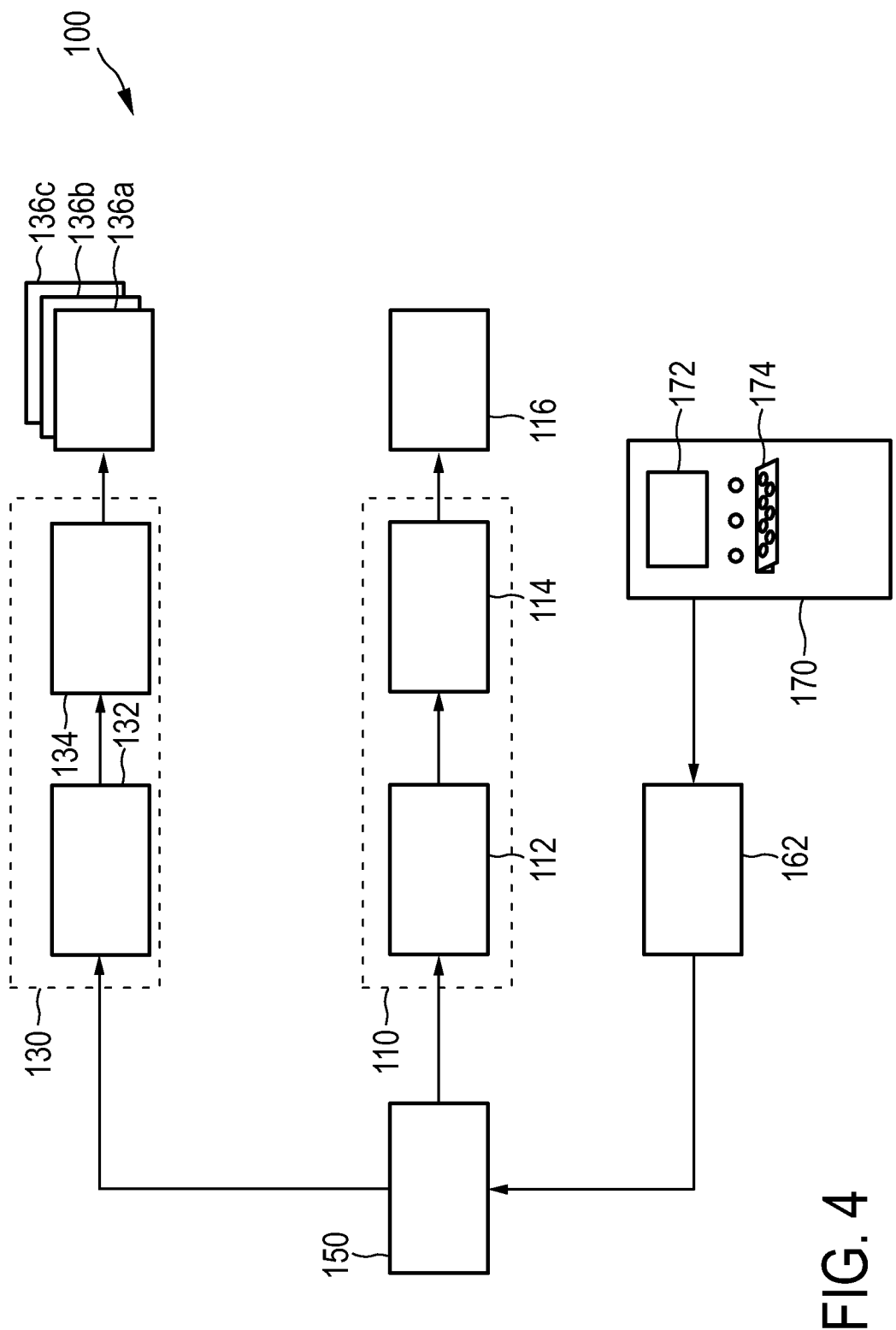
FIG. 4 shows a block diagram of a first embodiment of the MPI apparatus according to the present invention.
Figure 5:
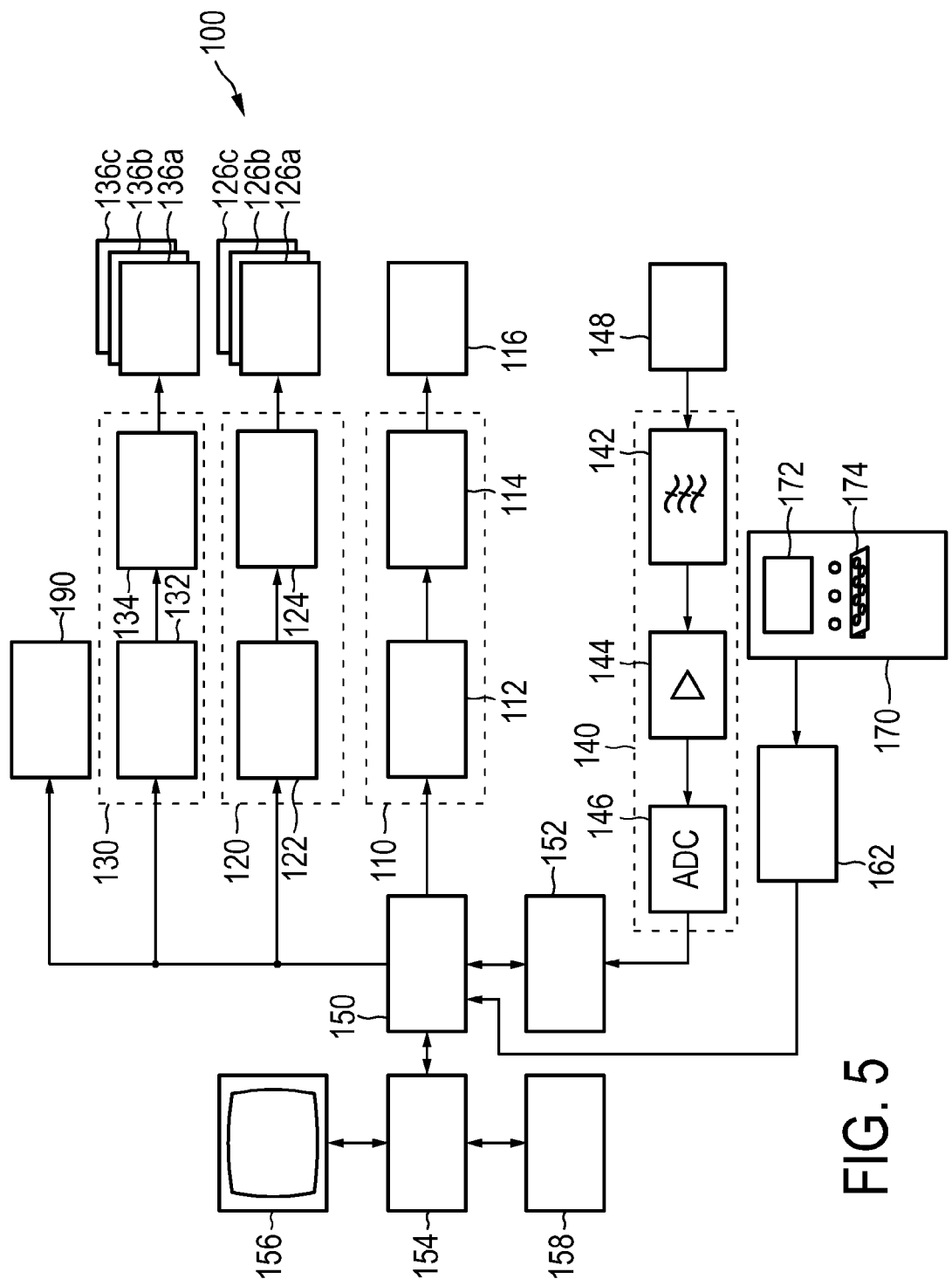
FIG. 5 shows a block diagram of a second embodiment of the MPI apparatus according to the present invention.

FIGS. 4 and 5 show a general block diagram of an MPI apparatus 10 according to a first and second embodiment of the present invention. The general principles of magnetic particle imaging explained above are valid and applicable to this embodiment as well, unless otherwise specified. For example the receiving and the processing means, which are, as already stated above, not obligatory for the apparatus according to the present invention, are not included in the first embodiment according to the present invention (see FIG. 4). The apparatus according to the first embodiment of the present invention thus does not make use of the MPI data acquisition and MPI imaging technique. The above mentioned focus means, which are also not obligatory for the present invention, are not included in the first embodiment as well. In contrast thereto the second embodiment of the present invention (shown in FIG. 5) includes all above mentioned means, the receiving means, the processing means and the focus means.

The first embodiment of the apparatus 100 shown in FIG. 4 comprises a set of various coils for generating the desired magnetic fields. First, the coils and their functions in a MPI mode shall be explained.

For generating the magnetic gradient selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field in the desired direction. Preferably, a DC current is provided. If the selection field coil elements 116 are arranged as opposed coils, e.g. on opposite sides of the field of view, the selection field currents of opposed coils are preferably oppositely oriented. The selection field signal generator unit 110 is controlled by a control unit 150, which preferably controls the selection field current generation 110 such that the sum of the field strength and the sum of the gradient strength of all spatial fractions of the selection field is maintained at a predefined level.

For generation of the magnetic drive field the apparatus 100 further comprises drive means comprising a subset of drive field (DF) coils, preferably comprising three pairs 136a, 136b, 136c of oppositely arranged drive field coil elements. The drive field coils are controlled by a drive field signal generator unit 130, preferably comprising a separate drive field signal generation subunit for each coil element (or at least each pair of coil elements) of said set of drive field coils 136a, 136b, 136c. Said drive field signal generator unit 130 comprises a drive field current source 132 (preferably including a current amplifier) and a filter 134 unit for providing a drive field current to the respective drive field coil 136a, 136b, 136c. The drive field current source 132 is adapted for generating an AC current and is also controlled by the control unit 150.

A control unit 150 is furthermore adapted for controlling said signal generator units 110, 130 to generate and provide control currents to the respective field coils to generate appropriate magnetic fields for moving the target element 60, 70 through the object in a direction instructed by movement commands, for placing the target element 60, 70 at the desired position within the object and for activating the active agent 61, 71 when the target element 60, 70 has reached said desired position. In the first embodiment shown in FIG. 4 the control unit 150 is in particular adapted for controlling the drive field signal generator unit 130 to generate and provide control currents to the drive field coils 136a, 136b, 136c to generate the RF field, which is necessary to move and place the target element 60, 70 at the desired position and to activate the active agent 61, 71 when the target element 60, 70 has reached the desired position. Said RF field is therefore superimposed over the drive field in the first embodiment of the present invention.

For inputting movement commands, an interface 162 is provided. Said interface 162 can be implemented in various ways. For instance, said interface 162 can be a user interface by which the user can manually input user commands, such as via a keyboard, a console, a joystick or a navigation tool, e.g. installed on a separate computer (not shown). In another implementation said interface 162 is an interface for a connection to an external device for movement control, such as a navigation unit, by use of which the movement of the target element 60, 70 has been planned in advance, e.g. based on image data of the object acquired in advance by another imaging modality, such as MR (magnetic resonance) or CT (computer tomography). The interface 162 then receives information about the desired movement and the desired position for placing the target element 60, 70 within the object, and the interface 162 or the control unit 150 is able to "translate" said commands into movement commands for the respective signal generator units (which is according to the first embodiment of the present invention the drive field signal generator unit 130).

Via the interface 162 movement commands are received from an external movement control unit 170 comprising a display 172, e.g. for displaying free-acquired image data of the object, and an operator control 174 for inserting control commands for planning the movement of the target element 60, 70.

In a practical intervention the surgeon will plan the intervention using the movement control unit 170. The navigation plan, which particularly includes the movement control commands and the desired position to place the target element 60, 70, is then provided via the interface 162 to the control unit 150 of the MPI apparatus 100. The control unit 150 then controls the movement of the target element 60, 70 within the object.

Hence, in effect, the apparatus according to the first embodiment of the present invention is able to move the target element 60, 70 through the object, in particular to control the direction of movement of the target element 60, 70, based on movement commands, and to control the placement of the target element 60, 70 at the desired position within the object irrespective in which form and by whom or what the movement commands have been provided.

Referring to FIG. 5, it can be seen that according to the second embodiment of the present invention an actuation means 190, focus means, receiving means and processing means are additionally included into the apparatus 100. The active agent 61, 71 is according to the second embodiment of the present invention activated via heating, which will be explained further below according to FIGS. 7a and 7b.

For generation of the above-mentioned RF field, actuation means 190 are provided in order to activate the active agent 61, 71 when the target element 60, 70 has reached its desired position. By means of this RF field the magnetic material 62, 72 of the target element 60, 70 in the field of view is heated, so that the active agent 61, 71 is locally activated. By means of this actuation means 190 the position in space of the two sub-zones 52, 54 in the field of view 28 is changed for so long and with such a frequency that the magnetic material 62, 72 of the target element 60, 70 is heated. When, due to the RF field, the position in space of the first sub-zone 52 is changed, the magnetization of the magnetic material 62, 72 of those target elements 60, 70, which are situated in the first sub-zone 52 or which migrate from the first 52 to the second sub-zone 54 or vice versa, is changed. Due to this change of magnetization, heat losses occur, for example, due to known hysteresis effects or hysteresis-like effects in the magnetic material or due to the initiation of particle movements, so that the temperature of the whole target element 60, 70 is increased. Because only a comparatively small amount of heat is produced when the magnetization is changed only once, the frequency of the RF field needs to be comparatively high in order to activate the active agent 61, 71. Apart from the frequency of the RF field, the total heating power also depends on the amplitude of the RF field, the magnetic material 62, 72 within the target element 60, 70 and the size of the target element 60, 70, respectively the size or the amount of the magnetic material 62, 72.

As can be seen from FIG. 5, according to the second embodiment of the present invention receiving means 148 are included in the apparatus 100. By use of these receiving means 148 detection signals can be acquired which then can be processed in order to reconstruct an image of the position and the surroundings of the target element 60, 70. By the help of this MPI imaging technique, the movement of the target element 60, 70 can be tracked so that at every time the current position of the target element 60, 70 can be checked visually and if necessary the movement defined in the navigation plan can be corrected at every time. This further simplifies the work of the surgeon and increases the accuracy of the placement of the target element 60, 70 within the object. In a practical intervention the movement of the target element 60, 70 can therefore be stopped in desired intervals so that the current position can be acquired on the basis of the detection signals provided by the receiving means 148. The signal detection shall therefore be explained in detail in the following.

The signal detection is besides the receiving means 148 additionally supported by a signal receiving unit 140, which receives signals detected by said receiving means 148. Said signal receiving unit 140 comprises a filter unit 142 for filtering the received detection signals. The aim of this filtering is to separate measured values from other, interfering signals. To this end, the filter unit 142 may be designed for example such that signals which have temporal frequencies that are smaller than the temporal frequencies with which the receiving means 148 are operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are lead to an image processing unit (also called reconstruction means) 152, which reconstructs the spatial distribution of the magnetic material 62, 72 of the target element 60, 70 from these signals and the respective position which the first sub-zone 52 of the first magnetic field in the examination area assumed during receipt of the respective signal and which the imaging processing unit 152 obtains from the control unit 150. The reconstructed spatial distribution of the magnetic material 62, 72 of the target element 60, 70 is finally transmitted via the control unit 150 to a computer 154 which displays it on a monitor 156. Thus, an image can be displayed showing the position of the target elements 60, 70 within the object.

As already mentioned above, the apparatus 100 according to the second embodiment of the present invention further comprises focus means. These focus means comprise a set of focus field (FF) coils, preferably three pairs 126a, 126b, 126c of oppositely arranged focus field coil elements. Said magnetic focus field is generally used for changing the position in space of the field of view 28. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field current unit 120 is also controlled by the control unit 150.

In summary this means that by additionally using focus means the position in space of the field of view 28 can be changed magnetically, whereas according to the first embodiment (without focus means), the object (e.g. the patient) needs to be moved manually in order to change the position in space of the field of view 28 with respect to the object.

Figure 6:
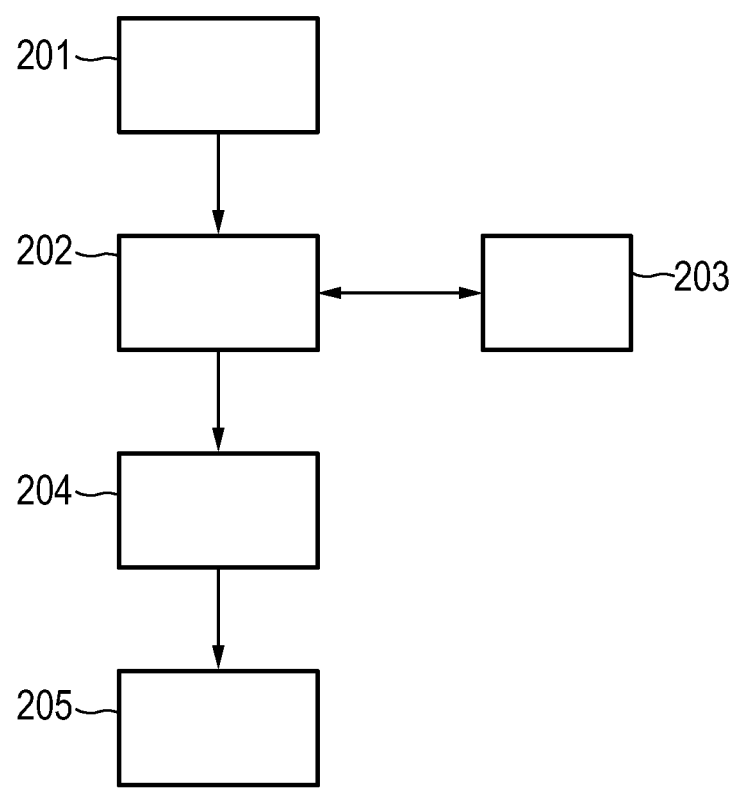
FIG. 6 shows a simplified block diagram of the method according to the present invention.

To summarize the whole procedure which is carried out by the apparatus 100 according to the present invention, the procedure respectively the method according to the present invention is visualized again in FIG. 6 in a simplified block diagram.

In a first step 201 a deposition plan for the active agents is defined by the physician. In case of brachytherapy or stroke treatments it is important to exactly define the positions and the dosage of the active agents (radioactive seeds respectively lysis drugs) which are to be deposited in the object. Additionally a navigation plan, in particular including movement control commands to steer the target elements 60, 70 through the object, can be defined.

According to the defined movement control commands the target elements 60, 70 are in step 202 actively moved through the object. For this movement the control unit 150 controls the signal generator units, preferably the drive or the focus field signal generator unit 130, 120, in order to generate and provide control currents to the respective field coils to generate appropriate magnetic fields. In this way, the target element 60, 70 is steered through the object simply by mechanical forces, i.e. no physical intervention of the object is necessary.

While moving the target element 60, 70 its current position is constantly tracked. For this tracking 203 the target element 60, 70 is stopped at desired intervals and its current position is acquired by applying an MPI sequence, preferably by moving the FFP along a trajectory through the area in which the target element 60, 70 might be currently located. The detection signals are then processed to get the current position of the target element 60, 70. Additionally the detection signals can be imaged using MPI image reconstruction technique. If necessary the movement direction can then be corrected based on the acquired tracking signal.

In step 204 the target element 60, 70 is finally placed at the desired position within the object. The target element 60, 70 can thereby be accurately positioned again using the drive or the focus field means.

In the last step 205 the active agent 61, 71, which is included in the target element 60, 70, is activated. This is preferably done by using an RF field which causes the magnetic material 62, 72 of the target element 60, 70 to oscillate and therefore produces heat. Due to this heating the coverage of the active agent 61, 71 might melt or liquefy so that the active agent 61, 71 can leave the target element 60, 70 and deploy its effect within the object.

Figure 7A:
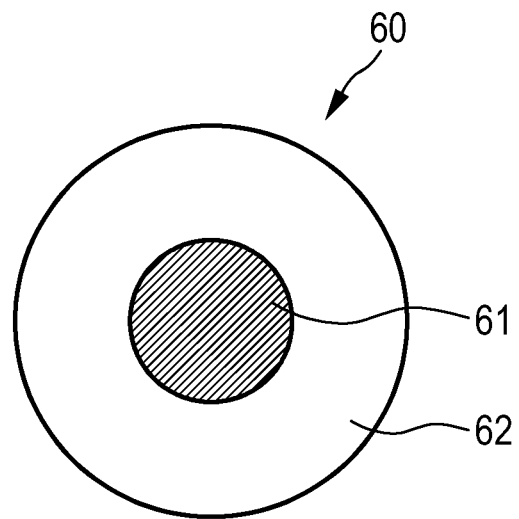
FIG. 7a shows a first embodiment of a target element according to the present invention.
Figure 7B:
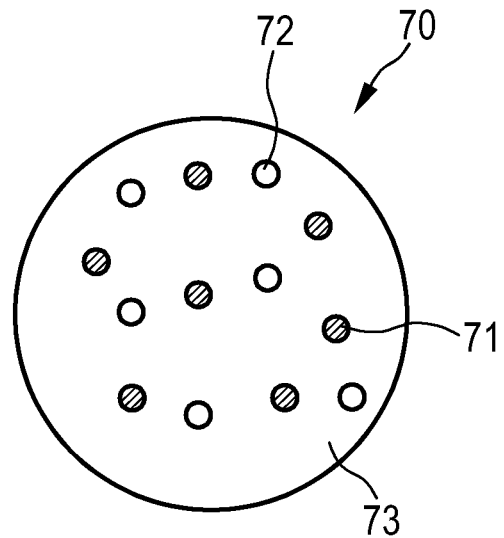
FIG. 7b shows a second embodiment of the target element according to the present invention.

In FIGS. 7a and 7b two different embodiments of the target element 60, 70 according to the present invention can be seen. In the first embodiment shown in FIG. 7a the target element 60 comprises a core which includes the active agent 61, whereby this core is covered by a magnetic material 62. As a magnetic material 62, usually a ferromagnetic material, such as an iron-nickel alloy, pure iron or a magnetic iron-oxide, is used. The advantage of pure-iron and iron-oxide is compared to the iron-nickel alloy its good decomposability characteristics in the human body. The active agent 61 can be, depending on the application, any substance, for example a radioactive seed used for brachytherapy treatments or a lysis drug used for stroke treatments. The activation of the active element 61 does not necessarily need to be caused by heat, it is also possible that, for example, the magnetic material 62 is solvable in the blood, so that the magnetic material 62 is dissolved in the blood after a certain time.

The same principle can also be applied for the second embodiment of the target element 70 according to the present invention. In contrast to the first embodiment, the magnetic material 72 and the active agent 71 are arranged in a different manner within the target element 70. The magnetic material and the active agent are hereby included in a matrix 73. This matrix 73 can, for example, consist of a lipid or another substance which can be easily liquefied or melted due to heating or which is solvable in the blood, respectively in the liquid in which the target element 70 is transported. All other physical principles already mentioned above concerning the first embodiment, also apply for the second embodiment of the target element 70 according to the present invention.

Furthermore, it has to be noted that the target element can have any geometrical form so that it does not necessarily have to have a spherical shape as shown in FIGS. 7a and 7b. The target element can for example have a spherical, ellipsoidal, helical, rectangular, rod-like or even cube-like form. The advantage of realizing the target element as a thin rod is that it can, due to its geometric form, contain a great amount of magnetic material and still blocking of an examined vessel can be avoided as long as the diameter of the vessel is greater than the diameter of the rod.

In summary the present invention provides a new method and apparatus for carrying out this method which make it possible to very accurately place target elements including active agents within an object and to very selectively activate these active agents. This technique can be particularly applied in treatments like brachytherapy or stroke treatments. In contrast to known techniques the presented technique has the main advantage that it is non-invasive, therefore less complicated for the surgeon and therefore also cheaper and shows an even higher accuracy than known techniques. Active agents like radioactive seeds or drugs can be placed within an object without the necessity of any surgical intervention. Due to the known MPI technique the magnetic field strengths that are used are even less compared to known medical imaging techniques like CT, MR or x-ray.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus for moving a target element, comprising:
   selection means comprising a selection field signal generator unit and selection field elements including selection field magnets or coils, for generating a magnetic selection field having a pattern in space of its magnetic field strength such that a first sub-zone having a low magnetic field strength and a second sub-zone having a higher magnetic field strength are formed in a field of view,
   drive means comprising a drive field signal generator unit and drive field coils for changing a position in space of the two sub-zones in the field of view by means of a magnetic drive field so that magnetization of magnetic material changes locally, said selection field elements and drive field coils are configured to generate magnetic fields which move a target element through an object in a direction that places the target element at a desired position within the object and activates an active agent when the target element has reached the desired position;

said target element comprising a magnetic material and an active agent, and control means for controlling said selection field signal generator unit and said drive field signal generator unit, said control means comprising:

an interface for inputting commands to provide a desired movement and/or a desired placement of the target element; and an electrical or mechanical control unit configured to receive commands from the interface, said control unit generates and provides control currents to the selection means and drive means which cause the selection field elements and drive field coils to generate appropriate magnetic fields which move the target element through the object in a direction instructed by the commands, wherein said magnetic fields place the target element at a desired position within the object and activate the active agent when the target element has reached said desired position.

2. An apparatus as claimed in claim 1, wherein actuation means are provided for changing the position in space of the two sub-zones in the field of view by means of a magnetic field for a sufficient period of time and/or with such a frequency that the magnetic material of the target element in the field, of view is heated so that the active agent is locally activated.

3. An apparatus as claimed in claim 2, wherein the actuation means are comprised of said drive means or a focus means comprising a focus field signal generator unit and focus field coils for changing the position in space of the field of view by means of a magnetic focus field.

4. An apparatus as claimed in claim 1, wherein actuation means are provided for generating a rotating magnetic field in the field of view which separates the active agent from the target element due to rotating forces.

5. An apparatus as claimed in claim 1, wherein focus means are provided which comprise a focus field signal generator unit and focus field coils for changing the position in space of the field, of view by means of a magnetic focus field.

6. An apparatus as claimed in claim 1, further comprising:

receiving means which comprise at least one signal receiving unit and at least one receiving coil for acquiring detection signals, wherein the detection signals depend on the magnetization in the field of view, and wherein the magnetization is influenced by the change in the position in space of the first and second sub-zone, and processing means for processing the detection signals acquired when appropriate magnetic fields are applied for determining the position of the target element within the object from the processed detection signals.

7. A method for moving a target element, comprising:

generating a magnetic selection field having a pattern in space of its magnetic field strength such that a first sub-zone having a low magnetic field strength and a second sub-zone having a higher magnetic field strength are formed in a field of view, changing a position in space of the two sub-zones in the field of view so that magnetization of magnetic material changes locally, moving the target element, comprising a magnetic material and an active agent, through an object in a direction instructed by movement commands to place the target element at a desired position within the object and activating the active agent when the target element has reached said desired position by controlling the generation of magnetic fields.

8. A non-transitory computer readable medium comprising a program code means, said program code means when executed, by a computer causes the computer to input commands into the interface to provide the desired movement and/or the desired placement of the target element in order to control generation of magnetic fields of the selection field signal generator unit and the drive field signal generator unit by a control unit of the apparatus as claimed in claim 1.

* * * * *